US012260943B2

(12) United States Patent
Makarkin et al.

(10) Patent No.: US 12,260,943 B2
(45) Date of Patent: Mar. 25, 2025

(54) DEFECTION PROPENSITY MODEL ARCHITECTURE WITH ADAPTIVE REMEDIATION

(71) Applicant: Evernorth Strategic Development, Inc., St. Louis, MO (US)

(72) Inventors: Alexi E. Makarkin, Ballwin, MO (US); Jay Summers, St. Louis, MO (US); Peter A. Rosomoff, Wildwood, MO (US); Christopher G. Bliss, St. Louis, MO (US); Matthew A. Hardin, Louisiana, MO (US); Xiaojian Wang, St. Louis, MO (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 379 days.

(21) Appl. No.: 17/586,117

(22) Filed: Jan. 27, 2022

(65) Prior Publication Data
US 2023/0238097 A1    Jul. 27, 2023

(51) Int. Cl.
*G06Q 30/02*  (2023.01)
*G06Q 30/0251*  (2023.01)
*G16H 20/10*  (2018.01)

(52) U.S. Cl.
CPC ......... *G16H 20/10* (2018.01); *G06Q 30/0251* (2013.01); *G06F 2218/12* (2023.01)

(58) Field of Classification Search
CPC ........ G16H 20/10; G16H 70/20; G16H 50/20; G06Q 30/0251; G06Q 10/08; G06Q 30/0202; G06Q 50/22; G06F 2218/12
See application file for complete search history.

(56) References Cited

U.S. PATENT DOCUMENTS

| 9,189,472 | B2 | 11/2015 | Medlock |
| 10,276,188 | B2 | 4/2019 | Feast |
| 10,607,241 | B2 | 3/2020 | Dalal |
| 10,866,848 | B2 | 12/2020 | Bridges |
| 11,521,047 | B1 * | 12/2022 | Reda ..................... G06N 3/084 |

(Continued)

OTHER PUBLICATIONS

Ng et al., Customer Retention vis Data Mining, 2000, Artificial Intelligence Review, vol. 14, pp. 569-590 (Year: 2000).*

(Continued)

*Primary Examiner* — John Van Bramer
(74) *Attorney, Agent, or Firm* — Miller Johnson

(57) ABSTRACT

A method for determining a defection probability includes receiving user data. The method also includes determining, from the user data, a set of features characterizing a likelihood of the user to change from the initial service channel to an alternative service channel. The method further includes generating an input encoding for the set of features. The method additionally includes determining, using a predictive model, a probability that indicates how likely the user is to change from the initial service channel, wherein the predictive model is trained to receive, as input, the input encoding and to generate, as output, a respective probability that indicates how likely a respective user is to change from the initial service channel to the alternative service channel. The method also includes determining whether the probability from the predictive model satisfies a defection threshold and selectively generating a remedial action based on the probability.

24 Claims, 11 Drawing Sheets

(56) References Cited

U.S. PATENT DOCUMENTS

| | | |
|---|---|---|
| 2001/0020229 A1 | 9/2001 | Lash |
| 2009/0287502 A1* | 11/2009 | Roberts ................. G06Q 40/08 |
| | | 705/3 |
| 2010/0057548 A1 | 3/2010 | Edwards |
| 2012/0130727 A1* | 5/2012 | Ahmed .................. G06Q 30/02 |
| | | 705/1.1 |
| 2014/0180974 A1 | 6/2014 | Kennel |
| 2014/0249865 A1 | 9/2014 | Ghani |
| 2017/0270546 A1 | 9/2017 | Kulkarni |
| 2020/0065835 A1* | 2/2020 | Manikandan ...... G06Q 30/0282 |
| 2020/0377342 A1* | 12/2020 | Michalke ................ B66B 21/10 |
| 2021/0011904 A1 | 1/2021 | James |

OTHER PUBLICATIONS

Buckinx et al., Customer base analysis: partial defection of behaviourally loyal clients in a non-contractual FMCG retail setting, 2005, European Journal of Operational Research, vol. 164, pp. 252-268 (Year: 2005).*

Mircheva et al., Building customer loyalty in Swedish pharmacy retail, May 2021, Lund University School of Economics Management, pp. 1-113 (Year: 2021).*

Bhavsar et al., A Comparative Study of Training Algorithms for Supervised Machine Learning, International Journal of Soft Computing and Engineering (IJSCE), Sep. 2012, vol. 2, Issue 4, pp. 74-81 (Year: 2012).*

* cited by examiner

Identifier 510

| Feature 512 | Feature Description | Type |
|---|---|---|
| 512a | Adjusted Retail Maintenance Prescription | Positive |
| 512b | Drug-Specific Defection Index | Positive |
| 512c | Mail Prescription Refill Number | Positive |
| 512d | Number of Prescriptions per Household | Positive |
| 512e | Number of Unique Maintenance Medications | Positive |
| 512f | Group-Level Maintenance Medication Ratio | Positive |
| 512g | Household-Level Adj. Maintenance Meds for Non-formulary Drugs At-Mail | Negative |
| 512h | Days' Supply Quantity for the Index Prescription At-Mail | Negative |
| 512i | Number of Web Logins in the Pre-Period | Negative |
| 512j | Age | Negative |
| 512k | Exclusive Home Delivery Flag | Negative |
| 512l | Mail Penetration % in the Pre-Period | Negative |
| 512m | Prescriber Specialty from the Index Mail Prescription | Positive/ Negative |

FIG. 5C

DEFECTION PROPENSITY MODEL ARCHITECTURE WITH ADAPTIVE REMEDIATION

FIELD

The present disclosure relates to multi-channel systems and more particularly to likelihood estimation modeling across channels.

BACKGROUND

Much like many industries today, healthcare systems have developed to provide different service channels (i.e., channels of trade) to deliver healthcare services and goods to consumers. These goods and services include drug therapies, such as prescriptions and other medications. Drug therapies are often prescribed by a healthcare provider (i.e., a physician) such as a doctor, nurse practitioner, physician assistant, pharmacist, and clinical psychiatrist, to a patient (i.e., consumer of healthcare services). Once prescribed a particular drug therapy, the patient fills the prescription and begins the drug therapy lifecycle. Traditionally, a patient would fill the prescription at a local brick and mortar pharmacy where the prescribing physician (also referred to as a prescriber) sent the prescription.

Yet as logistics have further developed and expanded to the healthcare ecosystem, a patient is now capable of using a home delivery system (i.e., "at-home delivery") as the service channel to receive their prescriptions instead of the traditional retail channel of trade (i.e., "at-retail"). This may be advantageous to many different types of patients: especially patients with chronic conditions and other ailments. Furthermore, some patients have difficulty filling prescriptions at retail locations such as retail pharmacies because of transportation issues or mobility issues. Although at-home delivery can alleviate some of these issues, drug therapies inherently have some degree of maintenance. That is, when the prescribed supply runs out, a prescription needs to be refilled. Due to this maintenance and other factors, a recipient of the drug therapy may cease the therapy or the drug therapy via the at-home delivery system. Therefore, to continue to provider efficient and/or effective healthcare in the drug therapy space, healthcare providers seek to understand a consumer's (i.e., patient's) behavior such as the consumer's propensity for various decisions regarding drug therapy.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

One aspect of the disclosure provides a computerized method for determining a defection probability. The method includes receiving user data for a user derived from at least one or more user interactions with an initial service channel. The method also includes determining a set of features from the user data where the set of features characterizes a likelihood of the user to change from the initial service channel to an alternative service channel. The method further includes generating an input encoding for the set of features from the user data. The method additionally includes determining, using a predictive model, a probability that indicates how likely the user is to change from the initial service channel to the alternative service channel, wherein the predictive model is trained to receive, as input, the input encoding and to generate, as output, a respective probability that indicates how likely a respective user is to change from the initial service channel to the alternative service channel. The method also includes determining that the probability from the predictive model satisfies a defection threshold and generating a remedial action based on the probability for the user prior to a service defection opportunity.

In some examples, the method also includes training the predictive model with a plurality of training samples. Each training sample corresponds to a recipient of one or more drug therapies via the initial service channel, and each training sample includes a training label that indicates whether the recipient defected from the initial service channel. In these examples, the training label may indicate that the recipient defected from the initial service channel in response to determining that the recipient changed from the initial service channel to the alternative service channel more than once during a period of time. In these examples, generating the plurality of training samples may occur by obtaining user data for a plurality of recipients of the one or more drug therapies via the initial service channel. For each respective recipient of the plurality of recipients, the method includes generating a training sample by: identifying a time horizon when the respective recipient received the one or more drug therapies via the initial service channel where the time horizon includes a first time period and a second time period; determining a training set of features from data for the respective recipient from the first time period; and determining whether the respective recipient changed from the initial service channel to the alternative service channel more than once during the second time period. When the respective recipient changed from the initial service channel to the alternative service channel more than once during the second time period, the method further includes generating the training label for the respective training sample indicating defection from the initial service channel. When the respective recipient failed to change from the initial service channel to the alternative service channel more than once during the second time period, the method also includes generating the training label for the respective training sample indicating no defection from the initial service channel.

Another aspect of the disclosure provides a system for determining a defection probability. The system includes data processing hardware and memory hardware. The memory hardware is configured to store instructions that, when executed by the data processing hardware, cause the data processing hardware to perform operations. The operations include receiving user data for a user derived from at least one or more user interactions with an initial service channel. The operations also include determining a set of features from the user data where the set of features characterizes a likelihood of the user to change from the initial service channel to an alternative service channel. The operations further include generating an input encoding for the set of features from the user data. The operations additionally include determining, using a predictive model, a probability that indicates how likely the user is to change from the initial service channel to the alternative service channel, wherein the predictive model is trained to receive, as input, the input encoding and to generate, as output, a respective probability that indicates how likely a respective user is to change from the initial service channel to the alternative service channel.

The operations also include determining that the probability from the predictive model satisfies a defection threshold and generating a remedial action based on the probability for the user prior to a service defection opportunity.

In some examples, the operations also include training the predictive model with a plurality of training samples. Each training sample corresponds to a recipient of one or more drug therapies via the initial service channel, and each training sample includes a training label that indicates whether the recipient defected from the initial service channel. In these examples, the training label may indicate that the recipient defected from the initial service channel in response to determining that the recipient changed from the initial service channel to the alternative service channel more than once during a period of time. In these examples, generating the plurality of training samples may occur by obtaining user data for a plurality of recipients of the one or more drug therapies via the initial service channel. For each respective recipient of the plurality of recipients, the operations include generating a training sample by: identifying a time horizon when the respective recipient received the one or more drug therapies via the initial service channel where the time horizon includes a first time period and a second time period; determining a training set of features from data for the respective recipient from the first time period; and determining whether the respective recipient changed from the initial service channel to the alternative service channel more than once during the second time period. When the respective recipient changed from the initial service channel to the alternative service channel more than once during the second time period, the operations further include generating the training label for the respective training sample indicating defection from the initial service channel. When the respective recipient failed to change from the initial service channel to the alternative service channel more than once during the second time period, the operations also include generating the training label for the respective training sample indicating no defection from the initial service channel.

Implementations of either the method or the system of the disclosure may include one or more of the following optional features. In some implementations, generating the input encoding includes, for each feature of the set of features, generating a value representing the likelihood of the user to change from the initial service channel to the alternative service channel based on the feature. Here, the value may be a logit value. In some configurations, generating the input encoding includes, for each feature of the set of features determining a feature bin corresponding to the feature from a plurality of feature bins and generating a value representing the likelihood of the user to chance from the initial service channel to the alternative service channel based on the feature bin. In some examples, the service defection opportunity corresponds to a renewal of a drug therapy and either the operations or the method further includes communicating the remedial action to the user prior to defection from the initial service channel by the user. In other examples, the service defection opportunity corresponds to a refill of a drug therapy and either the operations or the method further includes communicating the remedial action to the user prior to defection from the initial service channel by the user. Optionally, the set of features includes a first subset of positive features that indicate a positive correlation with the likelihood of the user to change from the initial service channel to the alternative service channel and a second subset of negative features that indicate a negative correlation with the likelihood of the user to change from the initial service channel to the alternative service channel.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 5C is a schematic view of example features for a prediction model.

In the drawings, reference numbers may be reused to identify similar and/or identical elements.

DETAILED DESCRIPTION

Introduction

Figure 1:
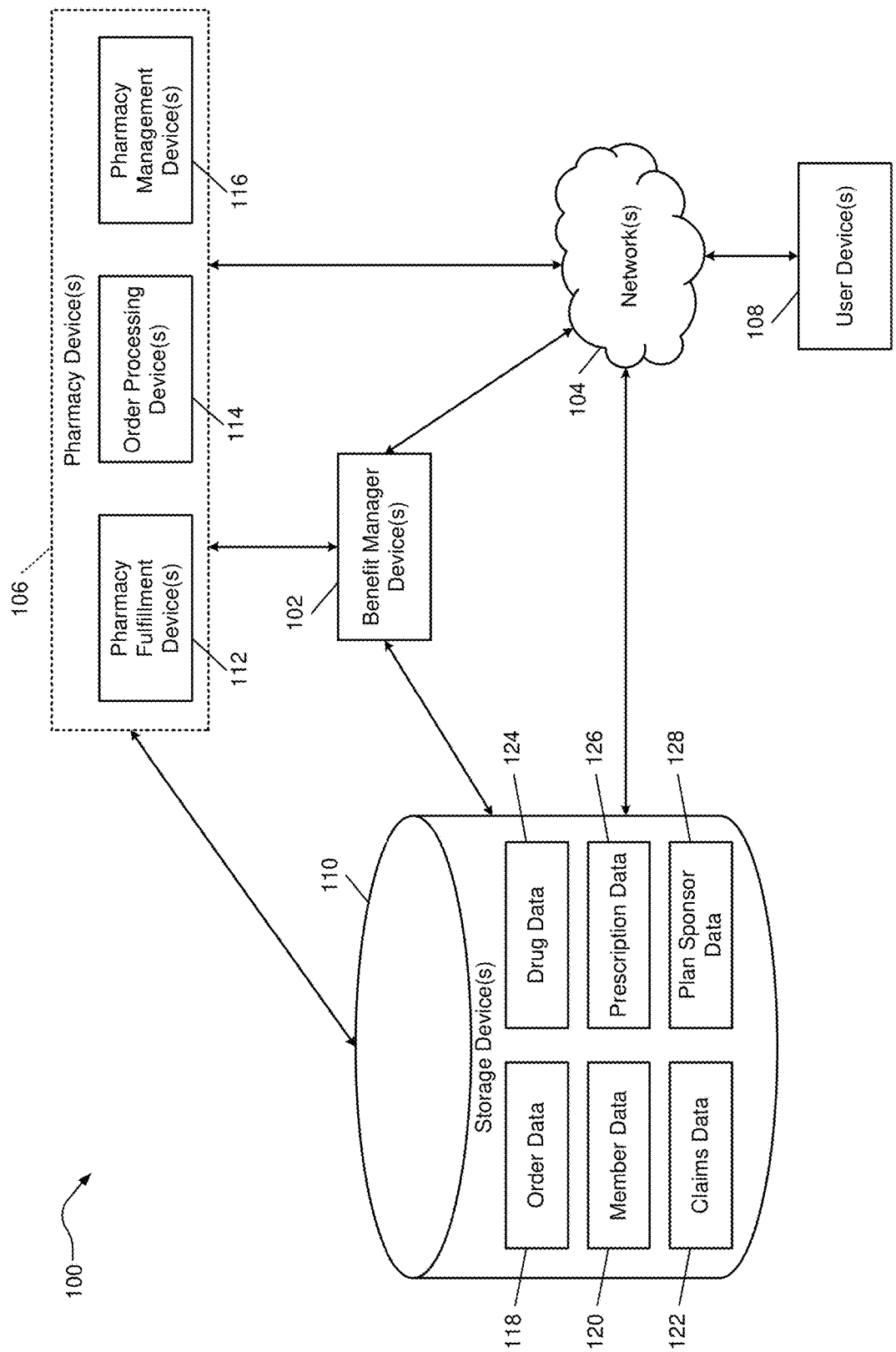
FIG. 1 is a functional block diagram of an example system including a high-volume pharmacy.

Since healthcare systems now provide their users (e.g., patients, consumers, customers) with options regarding how to receive their prescription drug therapies, each consumer inherently has some propensity to use one channel of trade as the supply channel for his/her prescription rather than another channel of trade as the supply channel. In other words, each consumer has a preference to use an at-home delivery system for prescriptions over a system where the consumer fills the prescription at a retail location (i.e., "at-retail") such as a local pharmacy or vice versa. This preference may be influenced by several factors including information about the consumer personally, his or her medical history, and/or his or her habits regarding medical care (e.g., behavior as it relates to prescriptions and drug therapies).

Furthermore, as consumers have been using at-home delivery systems, these consumers have generated consumer behavior data that can also provide insights into the consumer's propensity to use a particular supply channel. The consumer behavior data over time indicates that although many at-home system users continue using the at-home system for the delivery of their drug therapies, there are some users who switch between delivery channels. That is, a consumer who had been receiving his or her drug therapy via the at-home supply channel switches to the at-retail supply channel during his or her drug delivery history. The converse may also be true. That the consumer who had been receiving his or her drug therapy by picking up the drug therapy at a local pharmacy switches to use an at-home delivery system.

From the perspective of a healthcare provider who supports or provides the at-home delivery system, this healthcare provider has a greater concern for the consumer who leaves or defects from the at-home delivery system. Therefore, that healthcare provider has an interest in a user's propensity or likelihood to defect from the at-home delivery system. Here, defection refers to a user changing from a first supply channel (or initial supply channel) to a second supply channel. Yet behavior data also indicates there are generally two types of defection. A first type of defection, referred to as a temporary defection, is when a user, during his or her drug therapy history, changes from an initial supply channel to an alternative supply channel, but then back to the initial supply channel. This type of defection is referred to as temporary because, even though the user switches supply channels, this switch is temporary and the user returns to the original supply channel. For instance, an elderly woman may typically receive her drug therapy via at-home delivery, but a caretaker of the elderly woman decides to instead pick-up the drug therapy at retail when the drug therapy needed refilling. As another example, the at-home delivery system may be administered through a web-based application such as a web portal. In this example, the user realizes that he or she forgot to refill the drug therapy online (e.g., using the web portal) and that it will run out before it is capable of being delivered. In this situation, the user instead refills the drug therapy at-retail from the local pharmacy, but continues using the at-home delivery system for future drug therapy maintenance (e.g., subsequent refills).

In contrast, the second type of defection, referred to as permanent or persistent defection, is when a user, during his or her drug therapy history, changes from a first service channel to a second service channel, but then does not return to the original service channel. This type of defection is more concerning to an administrator of the at-home delivery system than a temporary defection. This concern stems from the that fact that a permanent defection may reflect issues with the at-home delivery system such as a poor consumer experience, logistic issues, or perhaps technical issues with a computing system being used to administer the at-home delivery system.

Furthermore, if there are issues, these issues may affect other users of the at-home delivery system and, potentially impact the users' health and well-being. For instance, defection can clinically affect a user. Often, drug prescriptions correspond to a drug therapy schedule for a particular medical condition of a user. If the user defects, there is a risk that this schedule is interrupted or potentially abandoned which may result in failure or poor effectiveness to treat the particular medical condition of the user. Additionally, at-home delivery systems tend to reduce or eliminate dispensing error because at-home delivery systems typically rely on dispensing automation rather than human dispensing (e.g., by an at-retail system). If the user defects to an at-retail system, the user eliminates the safeguards that can prevent human prescription errors.

Unfortunately, although permanent defection is the more concerning of the two types of defection, permanent defection can be difficult to quantify. That is, identifying something as permanent often means that its state cannot return to another state. But in the case of defection, the state of the user is capable of being entirely fluid where he or she may switch service channels at any time and is not tethered to one permanently. With this apparent issue in classifying a defection as permanent, the systems described herein instead classify a defection as a persistent defection when the circumstances of the defection satisfy defection criteria. In some examples, the system(s) classify a user's actions of changing service channels as persistent defection when a user's drug therapy delivery history indicates that an at-home delivery user refilled a drug therapy prescription two consecutive times at-retail over some designated length of time. In other words, by refilling the drug therapy consecutively (i.e., more than once), the actions of the user indicate a user defection that is more than temporary. Therefore, in this example, the defection criteria is two or more consecutive refills at-retail after initially using the at-home delivery system.

Since a user may switch deliver channels and this switching behavior may be of concern to service providers in a healthcare ecosystem (e.g., a service provider providing the at-home delivery service), there is a need to model and predict the propensity of the user to take such an action. That is, a need to model an at-home delivery user's likelihood of defection (also referred to as a defection probability). The defection model described herein seeks to address this need by generating a probability that a particular user will defect. Stated differently, the defection model intends to accurately model the probability of a complex human decision (i.e., defection). With a defection probability for a user, a service provider of the healthcare ecosystem can take one or more actions prior to defection that may benefit the healthcare ecosystem and the healthcare of the user.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, age, date of birth, address (including city, state, and zip code), telephone number, e-mail address, medical history, prescription drug history, etc. In various implementations, the prescription drug history may include a prior authorization claim history—including the total number of prior authorization claims, approved prior authorization claims, and denied prior authorization claims. In various implementations, the prescription drug history may include previously filled claims for the member, including a date of each filled claim, a dosage of each filled claim, the drug type for each filled claim, a prescriber associated with each filled claim, and whether the drug associated with each claim is on a formulary (e.g., a list of covered medication).

In various implementations, the medical history may include whether and/or how well each member adhered to one or more specific therapies. The member data 120 may also include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. In various implementations, the member data 120 may include an eligibility period for each member. For example, the eligibility period may include how long each member is eligible for coverage under the sponsored plan. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member). In various implementations, the claims data 122 may include a percentage of prior authorization cases for each prescriber that have been denied, and a percentage of prior authorization cases for each prescriber that have been approved.

The drug data 124 may include drug name (e.g., technical name and/or common name), other names by which the drug is known, active ingredients, an image of the drug (such as in pill form), etc. The drug data 124 may include information associated with a single medication or multiple medications. For example, the drug data 124 may include a numerical identifier for each drug, such as the U.S. Food and Drug Administration's (FDA) National Drug Code (NDC) for each drug.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
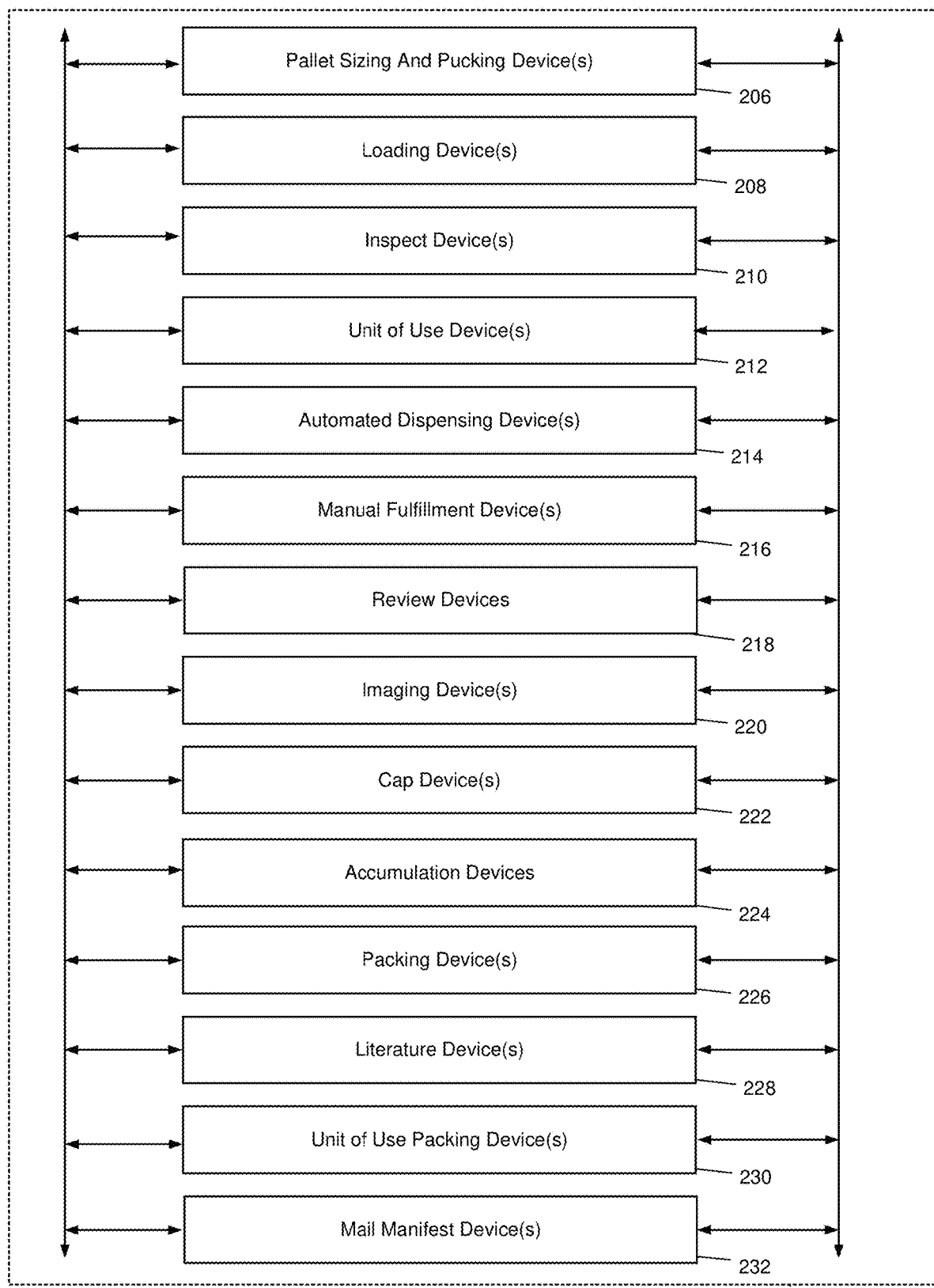
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
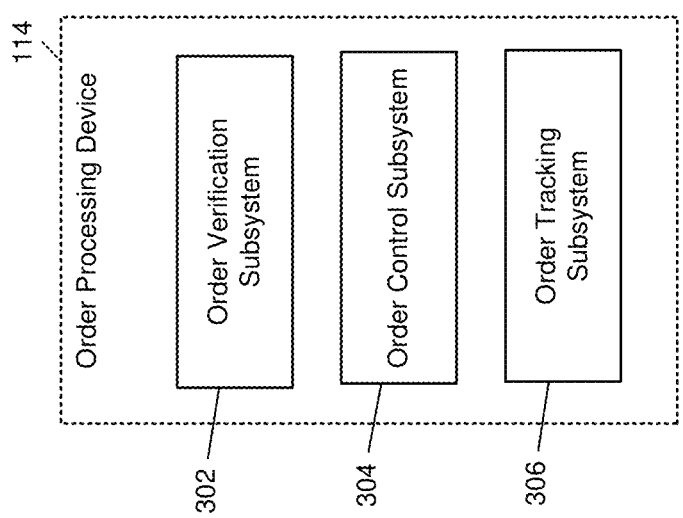
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Propensity Modeling

Figure 4:
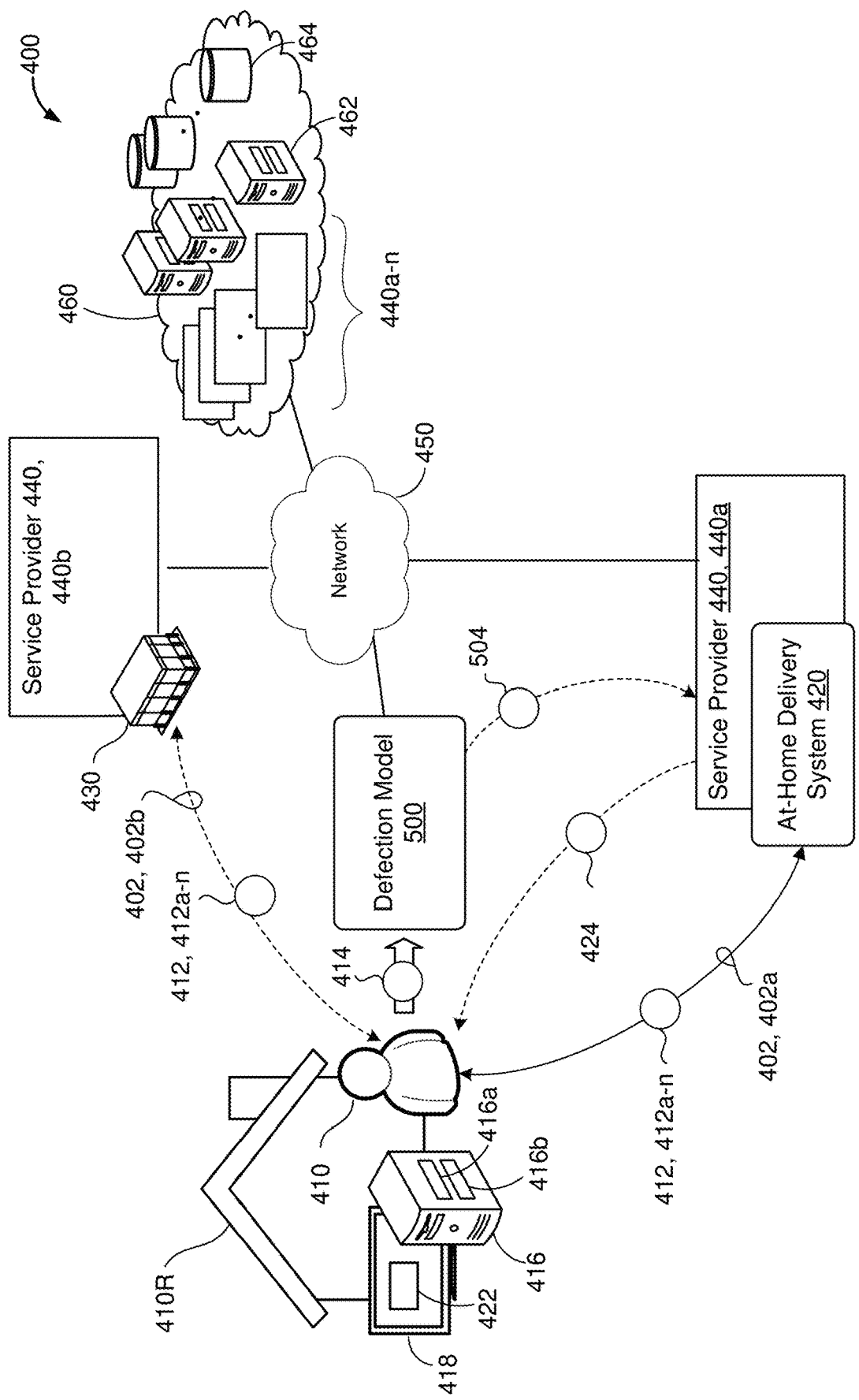
FIG. 4 is a schematic view of an example propensity model environment that includes a prediction model.

FIG. 4 is an example of a propensity modeling environment 400 (also referred to as environment 400). The environment 400 includes a user 410 who is using an at-home delivery system 420 (also referred to as an at-home delivery user 410) to receive one or more drug therapies 412 that have been prescribed to the user 410. Here, the at-home delivery system 420 functions to supply a drug therapy 412 to the user 410 at the user's home 410R or residence. Therefore, the at-home delivery system 420 establishes a first service channel 402, 402a (also referred to as a first supply channel) that logistically delivers the drug therapy 412 to the at-home delivery user 410 (e.g., without any logistic responsibility for the user 410). In some examples, the at-home delivery system 420 corresponds to some portion of the system 100 for a high-volume pharmacy (e.g., the pharmacy device(s) 106 and/or the benefits manager device (s) 102).

An at-home delivery system 420 is in contrast to a more traditional drug fulfillment process. Traditionally, a prescriber of the drug therapy 412 sent the prescription to a retailer such as a local pharmacy and the user 410 would pick-up or fill the drug therapy prescription at the local pharmacy retailer. This type of service system (or supply system) is therefore referred to as an "at-retail" system 430. That is, the user 410 physically procures the drug therapy 412 at a drug fulfillment retailer. The at-retail system 430 therefore uses a different service channel, shown as a second service channel 402, 402b than the at-home delivery system 420. For the second service channel 402b, the user 410 is generally responsible for the transportation logistics. Referring to FIG. 4, the at-retail system 430 is depicted as a local retail pharmacy.

In some examples, the user 410 is able to interface with the at-home delivery system 420 using a computing device 416 associated with the user 410 via a network 450 (e.g., similar to the network 104). In these examples, the at-home delivery system 420 may provide the user 410 with an application 422 (e.g., a web-based application such as a web portal) that functions as a drug delivery management interface. For instance, the user 410 uses his or her computing device 416 to access a web-application to coordinate at-home drug delivery (e.g., create/manage a drug delivery user account) and therapy drug maintenance events, such as refills, with the at home drug delivery system 420. As shown in FIG. 4, the computing device 416 includes a display 418 capable of rendering the application 422 as a graphical user interface, data processing hardware 416a, and memory hardware 416b storing instructions that, when executed on the data processing hardware 416a, allow the execution of the application 422 and any other electronic communication between the at-home delivery system 420 and the user 410. Some examples of user devices 110 include, but are not limited to, desktop computing devices and mobile computing devices, such as laptops, tablets, mobile phones (e.g., smart phones), and wearable computing devices (e.g., headsets and/or watches).

In some implementations, such as FIG. 4, the user 410 is recipient of healthcare services from one or more healthcare providers 440, 440a-n. Collectively, these healthcare providers 440 may form a healthcare network 460 to provide a wide array of healthcare services (e.g., inter-coordinated) such as medical services, pharmaceutical services, psychiatric services, dental services, etc. In this sense, both the at-home delivery system 420 and the at-retail system 430 may be managed, coordinated, or generally associated with a service provider 440 within the healthcare network 460 of the user 410 to provide in-network drug therapies 412 as well as out-of-network drug therapies 412 to the user 410. In this respect, FIG. 4 illustrates a first healthcare provider 440a associated with the at-home delivery system 420 and a second healthcare provider 440b associated with the at-retail system 430.

In some configurations, the healthcare network 460 is a remote system or distributed network. As a remote system, the healthcare network 460 as well as its service providers 440 may leverage remote resources, such as remote data processing hardware 462 and remote memory hardware 464, for the provision of various healthcare goods and services. For instance, the application 422 associated with the at-home delivery system 420 may be executable using, in part, remote resources (e.g., servers) of the remote system. Similarly, the remote memory hardware 464 may include databases storing information about at-home drug delivery users 410, such as drug therapies 412 associated with each user 410 and other user information (e.g., drug therapy history, user account information, and other information consented by the user for at-home drug delivery).

The environment 400 also includes a defection model 500 (also referred to as the model 500). The defection model 500 is broadly configured to receive user data 414 as an input 502 and to generate, as an output 504, a defection probability 532 for the user 410 associated with the user data 414. In other words, the model 500 may function to predict whether a user 410 has a propensity or likelihood to change from the at home delivery service channel 402a to another service channel 402, such as the second service channel 402b associated with the at-retail system 430. For example, the model 500 is a logistic regression model that predicts the likelihood that user 410 defects from the at-home delivery service channel 402a. In some examples, this likelihood may be determined whether or not the user 410 is currently using the at-home delivery system 420. For instance, since the model 500 receives user data 414 (e.g., drug therapy history or other medical/prescription information about the user) to make the determination of the user's defection probability, the model 500 does not necessarily require that the user 410 is currently using the at home delivery service channel 402a.

The at-home delivery system 420 may prefer to leverage the output 504 of the model 500 to understand whether its current users 410 may defect, but can also use the model 500 to determine a user's likelihood to use the at-home delivery system 420. For example, since a high probability 532 indicates that the user 410 is likely to defect from the at-home delivery service channel 402a to an alternative service channel 402b, the inverse is also true. That a low probability 532 from the model 500 indicates that the user 410 is unlikely to defect from the at-home delivery service channel 402a. In this respect, if a user 410 with a low probability is not a user of the at-home delivery system 420, the low probability indicates that this user 410 could be a strong candidate to use the at-home delivery system 420 for his or her drug therapy 412.

In some examples, when the at-home delivery system 420 is using the model 500 to evaluate potential candidates to use the services of the at-home delivery system 420, the at-home delivery system 420 employs a defection threshold set to a probability value that demarcates whether a particular user 410 is a strong candidate or a poor candidate for the system 420. For instance, the defection threshold is equal to 0.4 to indicate that a user 410 with a probability greater or equal to 0.4 has too strong of a likelihood to defect and is not a good candidate for the at-home delivery system 420. Whereas, if a respective user 410 has a probability less than 0.4, the likelihood of the user 410 to defect is considered low enough to be an acceptable target candidate for the at-home delivery system 420.

Figure 6A:
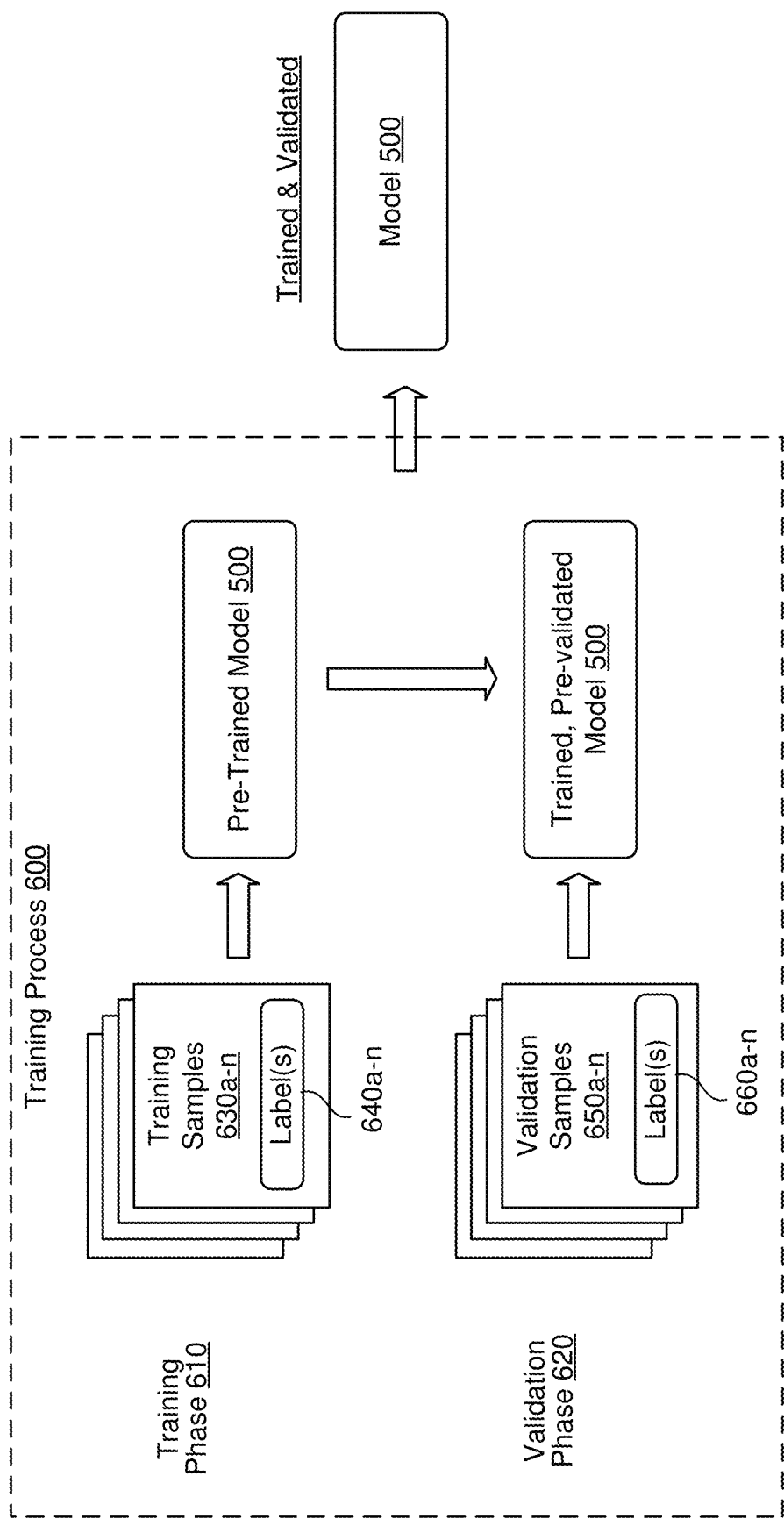
FIGS. 6A and 6B are schematic views of example training processes for training the prediction model.
Figure 6B:
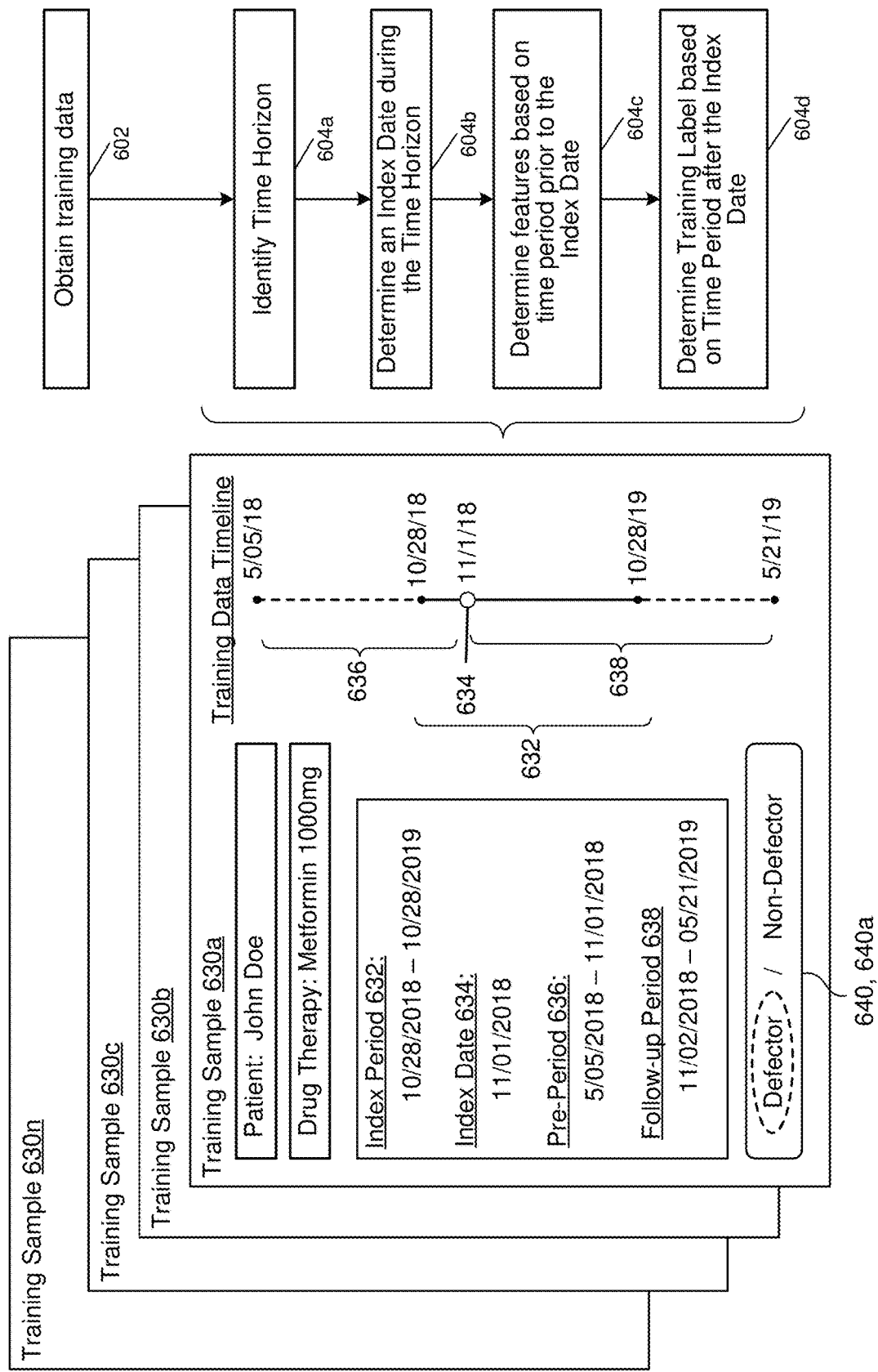

Although it is possible for the model 500 to generate any user's likelihood to defect from the at-home delivery service channel 402a, in some examples, the probability 532 may be considered to more accurately reflect the probability 532 for a current user 410 of the at-home delivery system 420 to defect. This may be the case because the model 500 is trained (e.g., as shown in FIGS. 6A and 6B) on supervised training samples (e.g., samples 630) where each training sample corresponds to a user 410 of the at-home delivery system 420 and is labeled based on whether that user 410 defects or does not defect over some period of time while being delivered his or her drug therapy(ies) 412 via the at-home delivery service channel 402a. In this sense, the model 500 may have some bias towards generating a defection probability 532 for a current user 410 of the at-home delivery system 420.

When modeling a current user 410 of the at-home delivery system 420, the defection threshold can identify customers that are at risk of defection. Here, when the model 500 generates a probability 532 for a current user 410 of the at-home delivery system 420 that satisfies the defection threshold (e.g., is greater than 0.4 in the previous example), the at-home delivery system 420 (or some other entity) may perform an action 424 to address and/or attempt to reduce the identified risk of defection. In other words, in response to generating a probability 532 for the current user 410 that satisfies the defection threshold (or defection criteria), the model 500 or an interrelated system (e.g., the at-home delivery system 420) generates a remedial action 424 that adapts to the defection risk for the user 410. For example, the at-home delivery system 420 (or a service provider 440 administering the at-home delivery system 420) communicates the action 424 to the user 410 as a type of intervention prior to an upcoming service defection opportunity (e.g., refill or renewal) for the drug therapy 412 of the user 410.

The remedial action 424 may be automated, manually communicated, or some combination of both. Some examples of remedial actions 424 include an email (e.g., automated email) to the user 410, a phone call (e.g., automated call) to the user 410, an offer or discount (or rebate) to refill the delivery of the drug therapy 412 via the at-home service channel 402a, and technical support to facilitate the refill with the at-home delivery system 420. Here, the email or phone call may function as a reminder to refill the delivery of the drug therapy 412 via the at-home service channel 402a. In some implementations, the remedial action 424 preliminarily prepares the refill for the user 410 via the at-home delivery system 420, but prompts the user 410 for consent or confirmation (i.e., requests approval from the user 410) to actually submit the refill for processing (i.e., fulfillment).

In some implementations, the type of action 424 performed in response to the defection probability 532 by a current user 410 of the at-home delivery system 420 depends on the particular defection probability 532 (e.g., a severity of the risk of defection). That is, instead of a single defection threshold, there may be multiple defection thresholds (e.g., defection criteria) forming bands or risk levels of defection. In this circumstance, each band or range of defection probabilities 532 may be setup such that when a defection probability 532 is within the range of defection probabilities 532 associated with a band, the at home-delivery system 420 or service provider 440 performs the action 424 (e.g., automatically performs the action 424) designated for that band. In this sense, the at-home delivery system 420 can tailor its response to the defection probability 532. For instance, there are three bands of defection probabilities 532. In this example, the first band (or range of defection probabilities 532) results in the communication of a first action 424 (e.g., an email to the user 410). The second band results in the communication of a second action 424 (e.g., a phone call to the user 410). The third band results in the communication of a third action 424 (e.g., a discount or exclusive offer). Here, the third band corresponds to the highest range of defection probabilities 532 while the first band corresponds to the lowest range of defection probabilities 532.

Additionally or alternatively, more than one action 424 may occur in response to a particular defection probability 532. For example, if the defection probability 532 satisfies the defection threshold or defection criteria, an action plan may occur where the action plan identifies one or more actions 424 to communicate to the user 410. In some configurations, the action plan includes timing information that designates when the one or more actions 424 associated with the action plan should/will occur. For example, the action plan dictates that the user 410 is first sent an email in response to the user's defection probability 532 satisfying the defection threshold or defection criteria. Then the action plan dictates that the user 410 is communicated a second action 424 some period of time after the first action 424 (e.g., the email). In some examples, the action plan dictates the timing of when action(s) 424 are communicated based on a time remaining until refill of one or more drug therapies 412 of the user 410.

Available actions 424 may be ranked based on their severity. For instance, actions 424 are ranked accordingly to severity based on their level of intrusion or intervention. An action 424 that does not solicit a user response may be considered to have a low level of intrusion/severity while an action 424 that acts on behalf of the user 424 or solicits a user response has a high level of intrusion/severity. In another approach, the actions 424 may be categorized as passive actions (e.g., informative actions 424) or active actions (e.g., perform some state change in the at-home delivery system 420 for the user 410).

With classified actions 424 (e.g., by severity and/or passive/active), the action 424 that occurs in response to a defection threshold or defection criteria may therefore be inversely proportional to the time remaining until refill or renewal. Stated differently, a user 410 generally defects when a service defection opportunity (i.e., a maintenance event) occurs such as a refill or a renewal. Therefore, to generate an action 424 that is inversely proportional to the time remaining before a service defection opportunity, the model 500 and/or the at-home delivery system 420 generates an action 424 that has a greater severity or is an active action when a less time remains before a service defection opportunity. For instance, if the user 410 is on the final refill for a drug therapy 412 and the defection probability 532 satisfies the defection threshold (e.g., exceeds or is greater than the defection threshold), the action 424 communicated to the user 410 may be technical support or submitting the renewal request for approval to the user 410 because these are more severe (e.g., more intrusive) intervention/remedial actions 424 than a more passive/less obtrusive automated email or automated phone call to the user 410.

The user 410 may receive the action 424 at the application 422 associated with the at-home delivery system 420. Upon receipt of the action 424, the user interface of the application 422 may transform to communicate the action 424 visually to the user 410. For instance, the user interface of the application 422 renders a display window that includes a notification for the action 424. In some configurations, the size, extents, or information conveyed in the notification for the action 424 depends on the severity of the action 424. In other words, if the action 424 is an automated email, the notification may be small window in a corner of the display 418. On the other hand, if the action 424 is a request to submit an auto-renewal of a drug therapy 412, the notification may be a pop-up window (e.g., overlain on a current window of the display 418) that is centered within the display 418 (e.g., in order to solicit the approval of the user 410 or ensure that the user 410 receives the notification of the action 424).

In some configurations, the model 500 is operating to determine defection probabilities 532 at a particular frequency for one or more users 410 of the at-home delivery system 420. For example, the model 500 is configured to generate a report of the defection probabilities 532 for users 410 of the at-home delivery system 420 daily, weekly, monthly, quarterly, semi-annually, annually, or some custom frequency. The report may be sorted by users 410 according to the severity of defection risk. That is, if the model 500 generates a report for five users 410, the report compiles the defection probabilities 532 for the five users 410 in an order that represents the user 410 with the greatest defection probability first and the lowest defection probability last. In some configurations, the model 500 or the at-home delivery system 420 only reports on defection probabilities that satisfy the defection threshold or defection criterial such that the at-home delivery system 420 is aware of the users 410 that are or will be receiving remedial action(s) 424 (e.g., automated remedial actions).

Referring to FIGS. 5A-5D, the model 500 generally includes an identifier 510, an encoder 520, and a predictor 530. The identifier 510 is configured to receive user data 414 for a user 410 being supplied a drug therapy 412 and to determine a set of features 512, 512a-n that characterize the likelihood of the user 410 to change from the initial service channel 402a for delivery of the drug therapy 412 to an alternative service channel 402b for the delivery of the drug therapy 412. Here, the user data 414 received as the model input 502 may correspond to any data relating to the user previously described such as order data 118, member data 120, claims data 122, drug data 124, prescription data 126, and/or plan sponsor data 128.

In some examples, the user data 414 is at least partially (or wholly) derived from at least one or more user interactions with the initial service channel 402a and/or one or more service providers 440 associated with the initial service channel 402a. Here, the user data 414 of relevance to the model 500 is user data 414 that contains information about the user, the user's prescriptions and drug therapy, and other healthcare related information about the user 410 shared with the at-home system 420 and/or one or more service providers 440 associated with the at home system 420 (e.g., healthcare network information for the user 410).

Figure 5A:
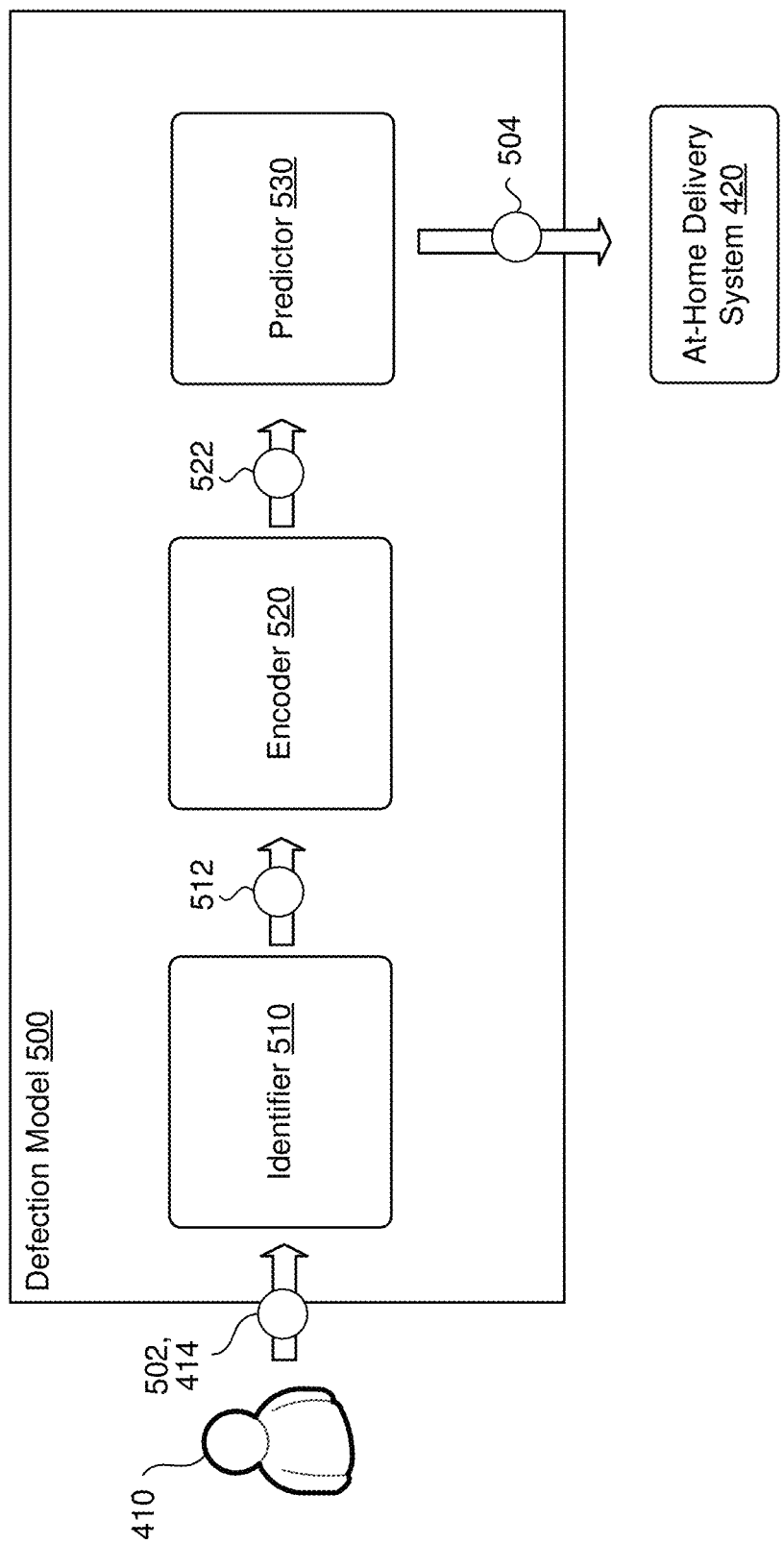
FIGS. 5A and 5B are schematic views of example prediction models, which may be deployed within the system of FIG. 4.
Figure 5B:
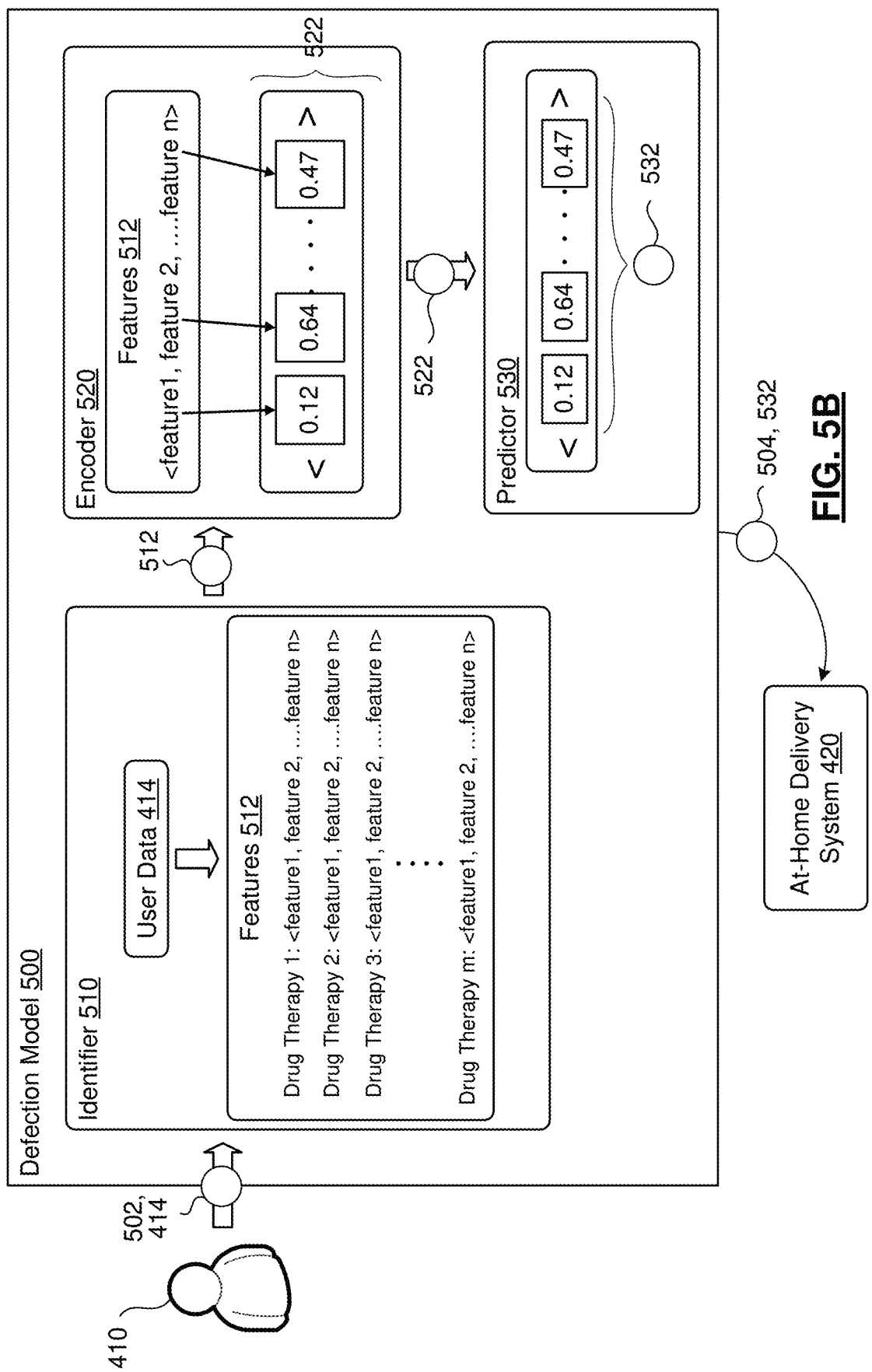

In some examples, the user 410 is being supplied more than one drug therapy 412. In these examples, the identifier 510 determines the set of features 512 for each drug therapy 412 of the user 410. For instance, FIG. 5B illustrates the user data 414 indicating that the user 410 has M number of drug therapies 412. Here, the identifier 510 generates N features 512 for each of the M therapies 412. That set of features 512 may form a matrix with the number of rows being equal to the number of drug therapies 512 (e.g., M rows) and the number of columns equal to the number of features 512 in the set of features 512 (e.g., N columns).

Features 512 can be derived from situations or facts about a user 410 that have been observed to impact some likelihood of defection for user 410. The features 512 may be configured in a variety of ways. In some examples, the features 512 are variables identified as positive features or negative features. A positive feature refers to a feature 512 that indicates a positive correlation with the likelihood of the user 410 to change from the at-home delivery service channel 402a to the alternative service channel 402b. On the other hand, a negative feature refers to a feature 512 that indicates a negative correlation with the likelihood of the user 410 to change from the at-home delivery service channel 402a to the alternative service channel 402b. A set of features 512 may therefore contain positive features, negative features, or some combination of both. For instance, the identifier 510 is configured to determine a set of features 512 from the user data 414 that includes a subset of positive features along with a subset of negative features.

FIG. 5C is an example of the features 512a-m that form the set of features 512. Here, there are six positive features 512, six negative features 512, and a feature 512 that could be either a positive feature 512 or a negative feature 512 depending on the circumstances. Although this example illustrates at least thirteen features 512 forming the set of features 512, different implementations of the model 500 may use more or less features 512 (e.g., five features, ten features, or twenty features) to generate the defection probability 532. The first feature 512a corresponds to a number of retail maintenance medications by the user 410. This feature 512 is a positive feature because users 410 with a greater frequency of retail experience are more likely to defect than users 410 with a lower frequency of retail experience. Therefore, the number of retail maintenance medications provides an indication of a user's existing interaction frequency with an at-retail system 430.

The second feature 512b corresponds to a drug-specific defection index. In some examples, the identifier 510 identifies each drug therapy 512 for a particular user 410 and determines a drug specific defection index for each drug therapy 512. Here, the drug defection index may be a preconfigured lookup table that includes the name of the drug therapy 512 and its corresponding defection index. The defection index may be a value that indicates how likely someone using the corresponding drug therapy 412 is to defect. For instance, drugs that correspond to specific therapeutic categories may tend to coincide with a higher risk of defection or vice versa (i.e., a lower risk of defection). Some examples of therapeutic categories that correspond to a high risk of defection include antidepressants, oral contraceptives, thyroid medications, seizure medications, hormone replacement drug therapies, attention deficit drug therapies, central nervous system drug therapies, and neurological drug therapies. On the other hand, some examples of therapeutic categories that corresponds to a low risk of defection are statin drug therapies (e.g., cholesterol lowering drugs), hypertension drug therapies, drug therapies for diabetes, anticoagulant drug therapies, ulcer drug therapies, urological drug therapies, and dermatological drug therapies. With these therapeutic categories corresponding to a particular risk level of defection, the drug-specific defection index may account for these therapeutic categories for the defection index of a particular drug therapy 412.

The third feature 512c is a mail prescription refill number. Generally speaking a drug therapy prescription includes a supply number (e.g., the number of pills or doses) and a refill number. Once the drug therapy has been refilled the specified number of times equal to the refill number, the user 410 will need to renew the prescription with a prescriber (e.g., generate another prescription). When the drug therapy 412 using the at-home delivery service channel 402a is closer to its need for renewal, there is a greater likelihood that the user 410 defects than when the drug therapy 412 is further from its need for renewal. Therefore, the refill number is a positive feature since the higher the refill number the closer the drug therapy 412 is to renewal and the greater the likelihood of defection.

The fourth feature 512d, which is a positive feature, is the number of prescriptions per household. There has generally been an observed trend that households of a user 410 with a higher number of prescriptions correspond to a user 410 who is more likely to defect than households of user 410 with a lower number of prescriptions.

The fifth feature 512e is the number of unique maintenance medications of the user 410. A maintenance medication or prescription is a drug therapy that is typically taken on a regular basis to treat a chronic condition. This feature 512e is a positive feature because there is a trend that users 410 with higher co-morbidities are more likely to defect than users 410 with lower co-morbidities. By including a count of the number of unique maintenance medications of the user 410, the fifth feature 512e can indicate whether the user 410 is likely to have a greater or lesser number of co-morbidities.

The sixth feature 512f is a group-level maintenance medication ratio. Prescribers or service providers 440 may place users 410 in group arrangements. These group arrangements may be benefit-designed grouping where users 410 in a group share similar member benefits. Some examples of these benefits are similar out-of-pockets expenses, similar copays, similar deductibles, similar drug formularies, similar delivery channels, or other similar benefit provisions. The identifier 510 may leverage these groupings to identify the ratio of drug therapies to maintenance drug therapies (i.e., drug therapies taken on a regular basis to treat a chronic condition). Similar to the fifth feature 512e where the greater the number of maintenance medications corresponds to a greater likelihood to defect, users 410 from groups with higher level of maintenance medication utilization are more likely to defect than users 410 from groups with a lower level of maintenance medication utilization.

The seventh feature 512g is the number of household-level maintenance medications for non-formulary drugs at-mail. In other words, how many chronically treating drug therapies are there in the household of the user 410 that are delivered at-mail and are non-formulary. A non-formulary drug therapy generally refers to a drug therapy that is not covered by the healthcare network of the user 410. Often these drug therapies are not covered (i.e., non-formulary) because the healthcare network covers a different drug therapy for treating the same condition. This seventh feature 512g is a negative feature because the greater the number of non-formulary maintenance medications at-mail in the household of the user 410, the less likely the user 410 is to defect.

The eighth feature 512h is the number of days for the supply quantity of a therapy drug 412 at-mail. Here, when a therapy drug 412 being delivered via the at-home delivery service channel 402a has a greater number of supply days, the user 410 of that drug therapy 412 is less likely to defect than when the drug therapy 412 has a lesser number of supply days. For example, drug therapies may be a 30-day, 60-day, or 90-day supply. A 30-day supply is less supply than a 90-day supply and therefore a user 410 with a drug therapy 412 having a 30-day supply is more likely to defect than a user 410 with a drug therapy 412 having a 90-day supply. In this respect, the number of days for the supply quantity of a therapy drug 412 at-mail is a negative feature.

The ninth feature 512i is a number of web logins for the user 410 during a particular time window (i.e., time period). This is because a user 410 who tends to be more apt to use the application 422 of the at-home delivery system 420 and logs into the application 422 often exhibits a greater likelihood to continue with use of the at-home delivery system 420 for his or her drug therapy(ies) 412. In this respect, the number of web logins for the user 410 during a particular period of time is a negative feature.

The tenth feature 512j is the age of the user 410. At-home delivery systems 420 have observed that the greater the age of the user 410, the lesser the likelihood that the user 410 will defect. This observation may stem from the fact that younger users 410 are less likely to have maintenance medications or be treating chronic conditions due to their age and are therefore more likely to be receiving drug therapy(ies) 412 that correspond to therapeutic categories that have a higher risk of defection (e.g., antidepressants, oral contraceptives, attention deficit medications, etc.). For this reason, the tenth feature 512j is a negative feature.

The eleventh feature 512k is whether the drug therapy 412 of the user 410 is exclusive to at-home delivery. In some examples, the drug therapy 412 being delivered to the user 410 via the at-home delivery supply channel 402a is considered exclusive to the supply channel 402a due to the cost. A drug therapy 412 that is exclusive to at-home delivery may have an at-retail offering, but the at-retail offering of the drug therapy 412 is at a much higher price. Here, the price difference between the at-home delivery of the drug therapy 412 and the at-retail delivery meets criteria such that the drug therapy 412 from the at-home delivery system 420 is considered to be exclusive to at-home delivery. This eleventh feature 512k is therefore a negative feature because a user 410 with an exclusive at-home drug therapy 412 has a lower likelihood to defect than a non-exclusive medication being delivered at-home to the user 410.

The twelfth feature 512l is a mail penetration percentage over a particular period of time. The mail penetration percentage is a percentage that indicates what percentage of the user's drug therapies 412 are being delivered via the at-home delivery service channel 402a. In other words, if the user 410 has ten of their ten medications being delivered via the at-home delivery supply channel 402a, this 100% penetration indicates that the user 410 is unlikely to defect compared to a user 410 who has one of their ten medications (i.e., 10%) being delivered via the at-home delivery service channel 402a. Based on this, the twelfth feature 512l is a negative feature.

The thirteenth feature 512m is the health specialty of a prescriber of the drug therapy 412. Similar to the therapeutic categories that tend to correlate to a greater likelihood or lesser likelihood of defection, the health specialty of the prescriber can also correlate to the defection likelihood. In some examples, the specialty of the prescriber may have a defection index that corresponds to the defection likelihood that has been designated for that prescriber's specialty. In these examples, the identifier 510 identifies the specialty of the prescriber and then determines the defection index for that specialty. The thirteenth feature 512a is then set equal to that particular defection index. Some examples of prescriber specialties that correlate to a high defection risk are neurology, pain management, addiction psychiatry, critical care, rehab care, advanced vascular, endocrinology and metabolism, and psychiatry. On the other hand, some examples of prescriber specialties that correlate to a low defection risk are family practice, internal medicine, cardiovascular, diabetes, pulmonary, and urology.

In some examples, the features 512 can corresponding to different categories of user data 414. Some examples of these categories include: demographic features or user-specific features that refer to particular characteristics of the user personally (e.g., the tenth feature 512j of age), prescription features that refer to certain details about the prescription such as does, supply quantity, refill number, prescriber (e.g., the eighth feature 512h of supply quantity or the thirteenth feature 512m of prescriber); benefit-related features that refer or characterize benefits that the user has (e.g., the sixth feature 512f of group-level medication ratio or the eleventh feature 512k of exclusive home delivery flag); household-related features that refer to details about the household of the user (e.g., the fourth feature 512d for the number of prescriptions per household); and user drug portfolio-related features that refer to details about the entire drug portfolio of the user 410 (e.g., the twelfth feature 512l for mail penetration % or the fifth feature 512e for the number of unique maintenance medications). Some or all of these categories of features 512 may be used to form the set of features 512 identified by the identifier 510.

Referring further to FIGS. 5A-5D, once the identifier 510 identifies the set of features 512 from the model input 502 (e.g., the user data 414), the identifier 510 communicates the set of features 512 to the encoder 520. The encoder 520 is configured to receive the set of features 512 and to generate an input encoding 522 (also referred to as an encoding 522 or encoded features 522) for the set of features 512. In some examples, to generate the encoding 522, the encoder 520 generates a value representing the likelihood of the user 410 to change from the at-home delivery service channel 402a to the alternative service channel 402b (e.g., the second service channel). For example, the encoder 520 generates an N dimensional vector for each drug therapy 412 associated with the user 410 where each dimension of the N dimensional vector corresponds to a feature 512 of the set of features 512. In some implementations, when the encoder 520 generates the encoding 522, the encoder 520 converts or determines a corresponding probability for each feature 512 such that the resulting encoding is a N dimensional vector where each dimension is a probability (e.g., a log likelihood or logit value) of a particular feature 512 from the set of features 512. For instance, FIG. 5B illustrates: feature1 being encoded into a value of 0.12; feature2 being encoded into a value of 0.64; and feature n being encoded into a value of 0.47. To further this example, feature1 may correspond an age feature 512j indicating that the user 410 is 36 years old. Based on a range of ages (e.g., 0-89), the encoder 520 interprets the age of 36 as a 0.17 value and represents that feature 512 as 0.17 in the resulting encoding 522.

Once the encoder 520 generates the encoding 522, the encoder 520 communicates the encoding 522 to the predictor 530. The predictor 530 is then configured to generate a defection probability 532 that indicates how likely the user 410 is to change from an initial service channel (e.g., the at-home delivery service channel 402a) to an alternative service channel (e.g., the at-retail service channel 402b). In other words, the predictor 530 interprets the encoding 522 corresponding to N number of features 512 and generates a single defection probability 532 based on the entirety of the encoded features 522. In some examples, the predictor 530 generates the single defection probability 532 as the sum product of each encoded feature (e.g., the encoding 522). In these examples, each encoded feature has a particular feature weight (e.g., a weighting coefficient) that indicates the encoded features contribution to the sum or defection probability 532. Here, these feature weights are particular to the feature itself and generally do not change based on the value of the encoded feature from the encoder 520. The model 500 then provides the defection probability 532 as the output of the model 500.

Figure 5D:
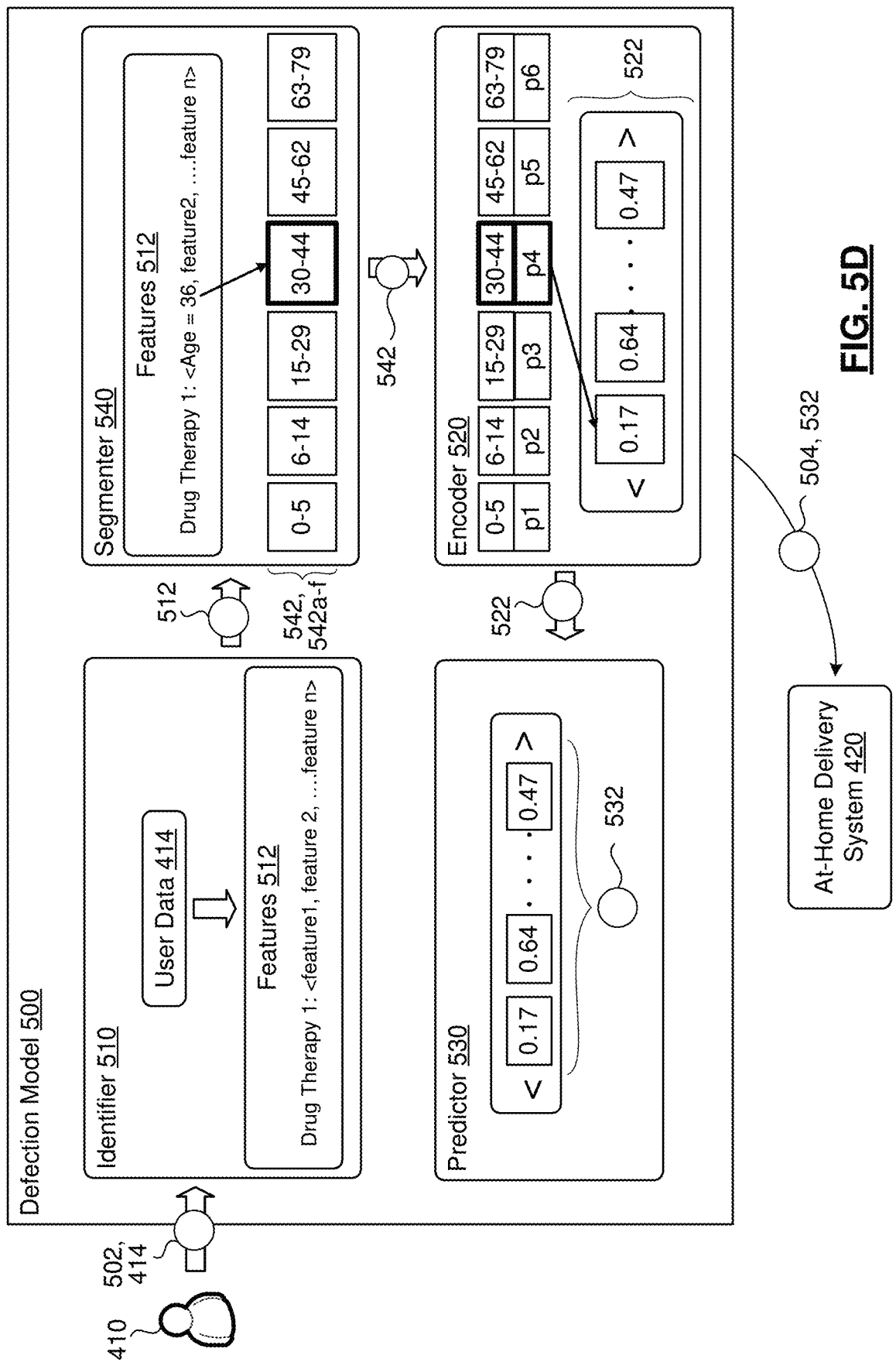
FIG. 5D is a schematic view of another example of a prediction model, which may be deployed within the system of FIG. 4.

In some configurations, such as FIG. 5D, the identifier 510 sends the features 512 to a segmenter 540 instead of the encoder 520. Here, the segmenter 540 is configured to identify (or generate) a plurality of feature bins 542, 542a-n corresponding to a particular type of feature 512. In some examples, the segmenter 540 generates X number of feature bins 542 for each type of feature 512. In other examples, the segmenter 540 dynamically determines the number of feature bins 542 based on the range of values possible for the particular feature 512 and/or the preferences of the designer of the model 500. For instance, although the age feature 512 includes ages ranging from 0-89, the refill number feature 512 (e.g., feature 512c) may be only five different values (e.g., 0, 1, 2, 3, or 4). Therefore, with a dynamic segmenter 540, the age feature 512 may map to fourteen feature bins 542 while the refill number feature 512 maps to five feature bins 542 or less.

With the plurality of feature bins 542 corresponding to the type of feature 512, the segmenter 540 then determines one of the feature bins 542 of the plurality of bins 542 that corresponds to the feature 512 itself (i.e., the value from the user data 414 that represents the feature 512). To illustrate, FIG. 5D depicts the age feature 512 corresponding to six feature bins 542a-f where each feature bin 542 is an age range. With the age feature 512 having a value of 36 (i.e., the user 410 is 36 years old), the segmenter 540 determines that the fourth feature bin 542d corresponds to the value of 36. The segmenter 540 converts (or maps) each feature 512 of the set of features 512 into the appropriate feature bins 542 and passes a vector of feature bins 542 for each drug therapy 412 of the user 410 to the encoder 520.

When the encoder 520 receives feature bin(s) 542 instead of the raw features 512, the encoder 520 instead determines an encoding for each feature bin 542 in order to generate the encoding 522. Referring to the prior example, since one of the feature bins 542 from the segmenter 540 corresponds to an age range from 30-44, the encoder 520 would generate the value of 0.17 (shown as the probability p4) for any age within that range because the encoder 520 is encoding the feature bin 542 from the segmenter 540 and not the underlying feature 512. Therefore, the age of 36 would result in the same encoding as an age of 43 since both ages are within the same feature bin 542. By mapping a feature 512 to a feature bin 542 and then encoding the feature bin 542, the model 500 may reduce its computational costs. Furthermore, by using a segmenter 540, the model 500 may avoid having to deal with features 512 with a large continuum of values and instead deal with discrete ranges. This discretization (i.e., the feature bins) can also be setup to reflect meaningful changes in the likelihood generated by the encoder 520. For instance, ages within the age range of 30-44 may not have a significant difference in the value generated by the encoder 520, but the difference in the value generated by the encoder 520 from the age of 29 to 30 or the age of 44 to 45 may result in a more significant value difference such that separate bins are generated for each of these ages.

Referring to FIGS. 6A and 6B, in order for the model 500 to determine the defection probability 532 from the encoding 522, the model 500 first undergoes a training process 600. Generally speaking, the training process 600 includes a training phase 610 and a validation phase 620. In the training phase 610, a pre-trained version of the model 500 is trained with a plurality of training samples 630a-n (generally referred to as training samples 630). These training samples 630 are supervised training samples 630 such that each training sample 630 includes a training label 640 that labels the training sample 630 as a defection sample or not a defection sample. Each training sample 630 corresponds to a recipient of one or more drug therapies 412 via the at-home delivery service channel 402a. The training label 640 therefore indicates whether the recipient defected from the at-home delivery service channel 402a after some period of time or did not defect from the at-home delivery service channel 402a during the period of time.

After the pre-trained model 500 has been trained with the plurality of training samples 630 in the training phase 610, the model 500 is a trained, but pre-validated version of the model 500. In other words, prior to inference (i.e., real data implementation) for the model 500, the validation phase 620 validates the performance of the model 500 and the model's ability to generate an accurate defection probability 532. In some configurations, in order to validate the trained model 500, the validation phase 620 determines whether the performance of the model 500 satisfies a validation confidence threshold (e.g., 95% confidence). For instance, the validation phase 620 may consider the model 500 validated when the model 500 correctly generates a defection probability 532 that corresponds to the defection label 660 of the validation samples 650. Typically, validation samples 650 are similar or the same as training samples 630 except that validation samples 650 are data samples that the model 500 has not seen during the training phase 610. In this respect, because the model 500 has not seen the validation samples 650, the trained, but pre-validated model 500 is not biased towards generating the correct defection probability 532 for these samples. Instead by preventing this bias, the validation phase 620 can ensure accurate validation of the trained model 500. When the validation phase 620 determines that the trained, but pre-validated model 500 performs successfully across the validation samples 650, the training process 600 certifies or considers the model 500 to trained, validated, and ready for deployment (i.e., inference).

FIG. 6B illustrates how the training process 600 generates each respective training sample 630 (or validation samples 650) corresponding to a recipient of one or more drug therapies 412 via the at-home delivery service channel 402a (i.e., a user 410 of the at-home delivery system 420). At operation 602, the training process 600 obtains data (referred to as training data) for the recipient. Training data is similar to user data 414 during actual deployment of the model 500 (i.e., inference/implementation) except that the training data is limited to a particular time horizon or index period 632. Therefore, after obtaining training data (or user data 414), the training process 600, at operation 604a, identifies the particular index period 632 that will correspond to the window of time used to generate the training sample 630. Generally speaking, the index period 632 includes a first time period that will form some portion of a pre-period 636 and a second time period that will form some portion of a follow-up period 638.

At operation 604b, the training process 600 determines an index date 634 during the index period 632. Since the training sample 630 is meant to simulate user data 414 when the model 500 is actually being used to generate the defection prediction 532, the training sample 630 includes a period of time having data that will form features 512 for the training sample 630 and a period of time from which the training process 600 will generate the training label 640. In some configurations, the training process 600 determines the index date 634 by identifying a date (i.e., a fill date) during the index period 632 when the recipient had a particular drug therapy 412 filled via the at-home delivery service channel 402a. This index date 634 therefore establishes a date that the recipient was definitely an at-home delivery user. Based on this index date 634, the training process 600 determines a pre-period 636 corresponding to a period prior to the index date 634 and a follow-up period 638 correspond to a period after the index date 634.

At operation 604c, the training process 600 determines features 512 based on the pre-period 636. For example, the training process 600 captures the training data for the recipient during the pre-period 636 and generates features 512 (also referred to as training features) for the training data from the pre-period 636. In some implementations, although the training process 600 identifies an index period 632 from the training data, the training data from the beginning of the index period 632 to the index date 634 is an insufficient data sample. For this reason, in these implementations, the training process 600 is setup such that the pre-period 636 is a designated period of time (e.g., 6 months) prior to the index date 634 regardless of the beginning of the index period 632. That is, the index period 632 may predominantly be used to identify the index date 634 and not necessarily limit the bounds of either of the pre-period 636 or the follow-up period 638.

At operation 604d, the training process 600 determines the training label 640 based on the follow-up period 638 after the index date 634. Much like the pre-period 636, the follow-up period 638 may not be bound by the limits of the index period 632 and instead be a time period of a designated length in order to allow the training process 600 to generate an accurate training label 640. For instance, the follow-up period 638 is six months long to determine whether the recipient corresponding to the training data defected during this period 638.

In some examples, to determine the training label 640, the training process 600 reviews the actions of the recipient during the follow-up period 638 to determine whether the recipient defected from the at-home delivery service channel 402a. In some configurations, the training process 600 determines whether the recipient defected during the follow-up period 638 by determining if one or more actions of the recipient satisfy the defection criteria. For instance, the defection criteria establishes that a defection is a persistent defection. With a persistent defection, the training process 600 generates the training label 640 to indicate that the recipient was a defector during the follow-up period 638 when the recipient changed from the at-home delivery service channel 402a to the alternative service channel 402b more than once during the follow-up period 638 (e.g., two consecutive times during the follow-up period 638). Here, if the recipient changed from the at-home delivery service channel 402a to the alternative service channel 402b only once or not at all for his or her drug therapy 412 during the follow-up period 638, the training process 600 generates the training label 640 to indicate that the recipient was not a defector.

FIG. 6B depicts an example of generating a first training sample 630a. In this example, the recipient is named John Doe. John Doe is supplied the drug therapy 412 of Metformin via the at-home delivery service channel 402a. The training process 600 obtains training data for John Doe that corresponds to the index period 632 of Oct. 28, 2018 to Oct. 28, 2019. During this index period 632, the training process 600 identifies that John Doe filled the Metformin prescription on Nov. 1, 2018.

In response to identifying the fill date of Nov. 1, 2018, the training process 600 equates the index date 634 to this fill date. The training process 600 then determines features 512 for John Doe based on the pre-period 636 of six months prior to the index date 634. The training process 600 additionally determines a first training label 640a for the first training sample 630a by determining whether John Doe defected during a follow-up period 638 after the index date 634. In this example, the follow-up period 638 is two hundred days after the index date 634 which means the follow-up period 638 begins on Nov. 2, 2018 and end on May 21, 2019. The training process 600 determines that John Doe defected during the follow-up period 638 and generates a label 640a indicating that John Doe is a defector on the first training sample 630a. This part of the training process 600 (e.g., operations 602-604) may then be repeated to generate a large number of training samples 630 as well as validation samples 650 and their corresponding labels 660. Following the generation of the training samples 630, the model 500 is trained to generate the defection prediction 532 as described and shown with respect to FIG. 6A.

Figure 7:
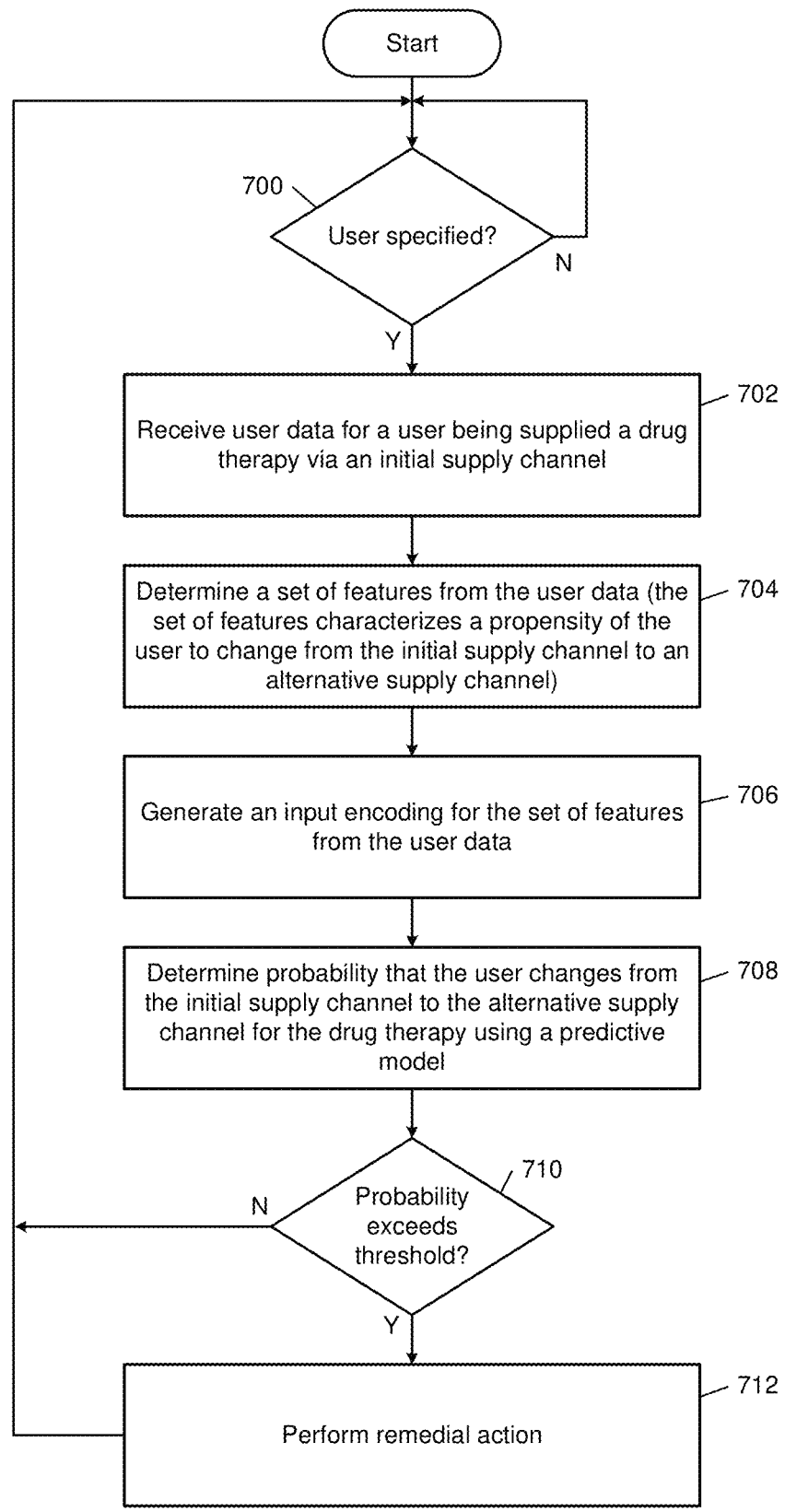
FIG. 7 is a flowchart of an example method including generation of a defection probability for a user.

FIG. 7 is a flowchart of an example method of generating a defection probability 532 using a predictive model 500. Control begins at 700, where control remains until a user 410 is specified. In various implementations, the user 410 is selected because they have been supplied a drug therapy 412 via an initial service channel (e.g., the at-home delivery service channel 402a). Once the user 410 is specified, control continues at 702.

At 702, control receives user data 414 for the user 410. At 704, control determines a set of features 512 from the user data 414. Here, the set of features 512 characterizes the likelihood of the user 410 changing from the initial service channel (e.g., the at-home delivery service channel 402a) to the alternative service channel (e.g., the at-retail service channel). At 706, control generates an input encoding 522 for the set of features 512 from the user data 414. At 708, control determines a defection probability 532, using the predictive model 500, that indicates a likelihood of the user 410 changing from the initial service channel (e.g., the at-home delivery service channel 402a) to the alternative service channel 402b for the drug therapy 412.

At 710, control compares the defection probability 532 to a threshold. The threshold may be adaptive and may be determined specifically for the user based on, for example, the user data 414. In response to the defection probability 532 exceeding a threshold, control transfers to 712; otherwise, control returns to 700. At 712, control initiates performance of one or more remedial actions, as specified above. In various implementations, a hierarchy of remedial actions may be performed. For example, the least processing-intensive remedial action may be attempted before, if success of the first remedial action cannot be verified, attempting the next-least-processing-intensive remedial action. After initiating remedial action (or a set of remedial actions), control returns to 700.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in a different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements as well as an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set—in other words, in some circumstances a "set" may have zero elements. The term "non-empty set" may be used to indicate exclusion of the empty set—in other words, a non-empty set will always have one or more elements. The term "subset" does not necessarily require a proper subset. In other words, a "subset" of a first set may be coextensive with (equal to) the first set. Further, the term "subset" does not necessarily exclude the empty set—in some circumstances a "subset" may have zero elements.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" can be replaced with the term "controller" or the term "circuit." In this application, the term "controller" can be replaced with the term "module."

The term "module" may refer to, be part of, or include processor hardware (shared, dedicated, or group) that executes code and memory hardware (shared, dedicated, or group) that stores code executed by the processor hardware.

The module may include one or more interface circuit(s). In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2020 (also known as the WIFI wireless networking standard) and IEEE Standard 802.3-2018 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

The memory hardware may also store data together with or separate from the code. Shared memory hardware encompasses a single memory device that stores some or all code from multiple modules. One example of shared memory hardware may be level 1 cache on or near a microprocessor die, which may store code from multiple modules. Another example of shared memory hardware may be persistent storage, such as a solid state drive (SSD) or magnetic hard disk drive (HDD), which may store code from multiple modules. Group memory hardware encompasses a memory device that, in combination with other memory devices, stores some or all code from one or more modules. One example of group memory hardware is a storage area network (SAN), which may store code of a particular module across multiple physical devices. Another example of group memory hardware is random access memory of each of a set of servers that, in combination, store code of a particular module.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A non-transitory computer-readable storage medium comprising processor-executable instructions, the instructions including:
   receiving user data for a user derived from at least one or more user interactions with an initial service channel;
   determining a set of features from the user data, wherein the set of features characterizes a likelihood of the user to change from the initial service channel to an alternative service channel;
   generating an input encoding for the set of features from the user data;
   training a predictive model with a plurality of training samples, wherein:
      the plurality of training samples corresponds to recipients of one or more drug therapies via the initial service channel, and
      the plurality of training samples includes training labels that indicate whether a respective recipient defected from the initial service channel;
   determining, using a predictive model, a probability that indicates how likely the user is to change from the initial service channel to the alternative service channel prior to a service defection opportunity, wherein the predictive model is trained to:
receive, as input, the input encoding, and
generate, as output, a respective probability that indicates how likely a respective user is to change from the initial service channel to the alternative service channel;
determining whether the probability from the predictive model satisfies a first defection threshold or a second defection threshold;
generating a remedial action based on the probability from the predictive model, wherein generating the remedial action includes:
in response to a determination that the probability from the predictive model has met the first defection threshold, automatically transmitting a first communication using a first communication protocol, and
in response to a determination that the probability from the predictive model has met the second defection threshold, automatically transmitting a second communication using a second communication protocol that is different from the first communication protocol; and
validating an accuracy of the predictive model, wherein validating the accuracy includes:
determining, based on a comparison of a set of predicted probabilities from the predictive model to a set of actual results associated with the set of predicted probabilities, whether an accuracy of the predictive model meets an accuracy threshold; and
in response to a determination that the accuracy of the predictive model has not met the accuracy threshold:
obtaining a set of data associated with a second recipient,
determining training labels for the set of data associated with the second recipient,
generating a second plurality of training samples based on the determined training labels and the set of data associated with the second recipient; and
retraining the predictive model with the second plurality of training samples to increase the accuracy of the predictive model.

2. The non-transitory computer-readable storage medium of claim 1, wherein a training label indicates that the respective recipient defected from the initial service channel in response to determining that the respective recipient changed from the initial service channel to the alternative service channel more than once during a period of time.

3. The non-transitory computer-readable storage medium of claim 1, wherein the instructions include generating the plurality of training samples by:
obtaining user data for a plurality of recipients of the one or more drug therapies via the initial service channel; and
for each respective recipient of the plurality of recipients, generating a training sample by:
identifying a time horizon when the respective recipient received the one or more drug therapies via the initial service channel, wherein the time horizon includes a first time period and a second time period;
determining a training set of features from data for the respective recipient from the first time period;
determining whether the respective recipient changed from the initial service channel to the alternative service channel more than once during the second time period;
when the respective recipient changed from the initial service channel to the alternative service channel more than once during the second time period, generating a training label for the training sample indicating defection from the initial service channel; and
when the respective recipient failed to change from the initial service channel to the alternative service channel more than once during the second time period, generating a training label for the training sample indicating no defection from the initial service channel.

4. The non-transitory computer-readable storage medium of claim 1, wherein generating the input encoding includes, for each feature of the set of features, generating a value representing the likelihood of the user to change from the initial service channel to the alternative service channel based on the feature.

5. The non-transitory computer-readable storage medium of claim 4, wherein the value is a logit value.

6. The non-transitory computer-readable storage medium of claim 1, wherein generating the input encoding includes, for each feature of the set of features:
determining a feature bin corresponding to the feature from a plurality of feature bins; and
generating a value representing the likelihood of the user to change from the initial service channel to the alternative service channel based on the feature bin.

7. The non-transitory computer-readable storage medium of claim 1, wherein:
the service defection opportunity corresponds to a renewal of a drug therapy, and
the instructions include communicating the remedial action to the user prior to defection from the initial service channel by the user.

8. The non-transitory computer-readable storage medium of claim 1, wherein:
the service defection opportunity corresponds to a refill of a drug therapy, and
the instructions include communicating the remedial action to the user prior to defection from the initial service channel by the user.

9. The non-transitory computer-readable storage medium of claim 1, wherein the set of features includes:
a first subset of positive features that indicate a positive correlation with the likelihood of the user to change from the initial service channel to the alternative service channel; and
a second subset of negative features that indicate a negative correlation with the likelihood of the user to change from the initial service channel to the alternative service channel.

10. The non-transitory computer-readable storage medium of claim 1, wherein:
the initial service channel is a delivery service channel, and
the alternative service channel is a user-pick-up service channel.

11. The non-transitory computer-readable storage medium of claim 1, wherein the instructions include:
determining whether the probability from the predictive model satisfies a third defection threshold, and
in response to a determination that the probability from the predictive model satisfies the third defection threshold:
identifying a prescription drug associated with the initial service channel, and fulfilling the prescription drug without operator intervention by:
  controlling movement of a set of containers relative to an automated dispensing device, and
  automatically dispensing, via the automated dispensing device, the prescription drug into a container of the set of containers.

12. The non-transitory computer-readable storage medium of claim 1, wherein generating the second plurality of training samples includes:
  identifying, from the set of data associated with the second recipient, an index date that corresponds to the second recipient receiving a drug therapy,
  identifying an index time period that includes the index date, and
  determining a set of features wherein:
    the set of features is based on the set of data associated with the second recipient,
    the set of features is based on data associated with the index time period,
    the set of features is based on data associated with dates before the index date, and
    the second plurality of training samples includes the set of features.

13. A system comprising:
  data processing hardware; and
  memory hardware in communication with the data processing hardware, wherein the memory hardware includes instructions that, when executed on the data processing hardware, perform operations, and wherein the operations include:
    receiving user data for a user derived from at least one or more user interactions with an initial service channel;
    determining a set of features from the user data, wherein the set of features characterizes a likelihood of the user to change from the initial service channel to an alternative service channel;
    generating an input encoding for the set of features from the user data;
    training a predictive model with a plurality of training samples, wherein:
      the plurality of training samples corresponds to recipients of one or more drug therapies via the initial service channel, and
      the plurality of training samples includes training labels that indicate whether a respective recipient defected from the initial service channel;
    determining, using a predictive model, a probability that indicates how likely the user is to change from the initial service channel to the alternative service channel prior to a service defection opportunity, wherein the predictive model is trained to:
      receive, as input, the input encoding, and
      generate, as output, a respective probability that indicates how likely a respective user is to change from the initial service channel to the alternative service channel;
    determining whether the probability from the predictive model satisfies a first defection threshold or a second defection threshold;
    generating a remedial action based on the probability from the predictive model, wherein generating the remedial action includes:
      in response to a determination that the probability from the predictive model has met the first defection threshold, automatically transmitting a first communication using a first communication protocol, and
      in response to a determination that the probability from the predictive model has met the second defection threshold, automatically transmitting a second communication using a second communication protocol that is different from the first communication protocol; and
    validating an accuracy of the predictive model, wherein validating the accuracy includes:
      determining, based on a comparison of a set of predicted probabilities from the predictive model to a set of actual results associated with the set of predicted probabilities, whether an accuracy of the predictive model meets an accuracy threshold; and
      in response to a determination that the accuracy of the predictive model has not met the accuracy threshold:
        obtaining a set of data associated with a second recipient,
        determining training labels for the set of data associated with the second recipient,
        generating a second plurality of training samples based on the determined training labels and the set of data associated with the second recipient; and
        retraining the predictive model with a second plurality of training samples to increase the accuracy of the predictive model.

14. The system of claim 13, wherein a training label indicates that the respective recipient defected from the initial service channel in response to determining that the respective recipient changed from the initial service channel to the alternative service channel more than once during a period of time.

15. The system of claim 13, wherein the operations include generating the plurality of training samples by:
  obtaining user data for a plurality of recipients of the one or more drug therapies via the initial service channel; and
  for each respective recipient of the plurality of recipients, generating a training sample by:
    identifying a time horizon when the respective recipient received the one or more drug therapies via the initial service channel, wherein the time horizon includes a first time period and a second time period;
    determining a training set of features from data for the respective recipient from the first time period;
    determining whether the respective recipient changed from the initial service channel to the alternative service channel more than once during the second time period;
    when the respective recipient changed from the initial service channel to the alternative service channel more than once during the second time period, generating a training label for the training sample indicating defection from the initial service channel; and
    when the respective recipient failed to change from the initial service channel to the alternative service channel more than once during the second time period, generating a training label for the training sample indicating no defection from the initial service channel.

16. The system of claim 13, wherein generating the input encoding includes, for each feature of the set of features, generating a value representing the likelihood of the user to change from the initial service channel to the alternative service channel based on the feature.

17. The system of claim 16, wherein the value is a logit value.

18. The system of claim 13, wherein generating the input encoding includes, for each feature of the set of features:
   determining a feature bin corresponding to the feature from a plurality of feature bins; and
   generating a value representing the likelihood of the user to change from the initial service channel to the alternative service channel based on the feature bin.

19. The system of claim 13, wherein:
   the service defection opportunity corresponds to a renewal of a drug therapy, and
   the operations include communicating the remedial action to the user prior to defection from the initial service channel by the user.

20. The system of claim 13, wherein:
   the service defection opportunity corresponds to a refill of a drug therapy, and
   the operations include communicating the remedial action to the user prior to defection from the initial service channel by the user.

21. The system of claim 13, wherein the set of features includes:
   a first subset of positive features that indicate a positive correlation with the likelihood of the user to change from the initial service channel to the alternative service channel; and
   a second subset of negative features that indicate a negative correlation with the likelihood of the user to change from the initial service channel to the alternative service channel.

22. The system of claim 13, wherein:
   the initial service channel is a delivery service channel, and
   the alternative service channel is a user-pick-up service channel.

23. The system of claim 13, wherein the operations include:
   determining whether the probability from the predictive model satisfies a third defection threshold, and
   in response to a determination that the probability from the predictive model satisfies the third defection threshold:
      identifying a prescription drug associated with the initial service channel, and
      fulfilling the prescription drug without operator intervention by:
         controlling movement of a set of containers relative to an automated dispensing device, and
         automatically dispensing, via the automated dispensing device, the prescription drug into a container of the set of containers.

24. The system of claim 13, wherein generating the second plurality of training samples includes:
   identifying, from the set of data associated with the second recipient, an index date that corresponds to the second recipient receiving a drug therapy,
   identifying an index time period that includes the index date, and
   determining a set of features, wherein:
      the set of features is based on the set of data associated with the second recipient,
      the set of features is based on data associated with the index time period,
      the set of features is based on data associated with dates before the index date, and
      the second plurality of training samples includes the set of features.

* * * * *